(12) United States Patent
Shinozaki

(10) Patent No.: US 10,932,669 B2
(45) Date of Patent: Mar. 2, 2021

(54) EXAMINATION APPARATUS, METHOD FOR CONTROLLING EXAMINATION APPARATUS, SYSTEM, LIGHT GUIDE, AND SCALE

(71) Applicant: Derma Medical Inc., Yokohama (JP)

(72) Inventor: Takashi Shinozaki, Yokohama (JP)

(73) Assignee: Derma Medical Inc., Yokohama (JP)

( * ) Notice: Subject to any disclaimer, the term of this patent is extended or adjusted under 35 U.S.C. 154(b) by 30 days.

(21) Appl. No.: 16/306,517

(22) PCT Filed: Jan. 9, 2018

(86) PCT No.: PCT/JP2018/000204
§ 371 (c)(1),
(2) Date: Nov. 30, 2018

(87) PCT Pub. No.: WO2018/135337
PCT Pub. Date: Jul. 26, 2018

(65) Prior Publication Data
US 2019/0159678 A1 May 30, 2019

(30) Foreign Application Priority Data
Jan. 17, 2017 (JP) .............................. JP2017-005866

(51) Int. Cl.
*G06K 9/00* (2006.01)
*A61B 5/00* (2006.01)
(Continued)

(52) U.S. Cl.
CPC .............. *A61B 5/0077* (2013.01); *A61B 5/00* (2013.01); *A61B 5/441* (2013.01); *A61B 10/00* (2013.01);
(Continued)

(58) Field of Classification Search
CPC .................................................. A61B 5/0077
(Continued)

(56) References Cited

U.S. PATENT DOCUMENTS

2002/0054661 A1\* 5/2002 Anderson ............ G01N 23/223
378/44
2005/0159662 A1\* 7/2005 Imanishi .............. A61B 3/1025
600/473

(Continued)

FOREIGN PATENT DOCUMENTS

| JP | 2005-192944 | 7/2005 |
| JP | 2014-050707 | 3/2014 |

(Continued)

OTHER PUBLICATIONS

International Search Report for International Application No. PCT/JP2018/000204, dated Apr. 24, 2018, in 5 pages.

*Primary Examiner* — Stephen P Coleman
(74) *Attorney, Agent, or Firm* — Knobbe, Martens, Olson & Bear, LLP

(57) ABSTRACT

[Technical Problem]
To provide an inspection device for inspecting a tissue using reflected light from a tissue, and a control method, a system, a light guide, and a scale of the inspection device.
[Solution to Problem]
An inspection device 100 of the present invention comprises an imaging device 106 and an inspection module 115 for allowing the imaging device 106 to take a tissue image. The inspection module 115 includes an objective lens 104 for focusing reflected light from a tissue to the imaging device 106; a plurality of LEDs 103*a* for surrounding the optic axis of the objective lens 104 and exposing light to the tissue; a circular polarization filter 102 comprising polarization state-regulating parts 102*a* for exposing the light from the LEDs 103*a* to the tissue directly or as circularly polarized light;

(Continued)

and an alignment mechanism 110a for aligning the polarization state-regulating part 102a with the position of the LED 103a.

9 Claims, 17 Drawing Sheets

(51) Int. Cl.
  *G06T 7/00* (2017.01)
  *F21V 9/14* (2006.01)
  *A61B 10/00* (2006.01)
  *F21W 131/20* (2006.01)
  *F21Y 115/10* (2016.01)

(52) U.S. Cl.
  CPC .............. *F21V 9/14* (2013.01); *G06T 7/0012* (2013.01); *F21W 2131/20* (2013.01); *F21Y 2115/10* (2016.08); *G06T 2207/30088* (2013.01)

(58) Field of Classification Search
  USPC ........................................................ 382/128
  See application file for complete search history.

(56) References Cited

U.S. PATENT DOCUMENTS

| | | | |
|---|---|---|---|
| 2006/0192854 A1* | 8/2006 | Perlman | ................... G01S 17/87 |
| | | | 348/154 |
| 2008/0275315 A1 | 11/2008 | Oka et al. | |
| 2015/0036311 A1 | 2/2015 | Mullani | |
| 2016/0338587 A1* | 11/2016 | Gupta | ...................... A61B 3/14 |

FOREIGN PATENT DOCUMENTS

| | | |
|---|---|---|
| JP | 2014-239759 | 12/2014 |
| JP | 2015-188579 | 11/2015 |
| JP | 2015-188590 | 11/2015 |
| JP | 2016-214552 | 12/2016 |
| WO | WO 2005/065534 | 7/2005 |

* cited by examiner

1200

| Patient's personal identification information | date1 | date2 | date3 | date4 |
|---|---|---|---|---|
| A | Direct mode<br>Polarization mode | Direct mode<br>Polarization mode | | |
| B | Direct mode<br>Polarization mode | Direct mode<br>Polarization mode | Direct mode<br>Polarization mode | |
| C | Direct mode<br>Polarization mode | | | |
| D | Direct mode<br>Polarization mode | | | |
| ⋮ | ⋮ | ⋮ | ⋮ | ⋮ |

*FIG. 12*

EXAMINATION APPARATUS, METHOD FOR CONTROLLING EXAMINATION APPARATUS, SYSTEM, LIGHT GUIDE, AND SCALE

TECHNICAL FIELD

The present invention relates to an inspection device, a control method, system, light guide and scale of the inspection device, and more particularly relates to an inspection device for inspecting a skin, a mucosa, an epithelial cell structure using a reflected light from a skin; and a control method, a system, a light guide and a scale of the inspection device.

BACKGROUND ART

Digital dermoscopes have been conventionally and regularly known as devices and inspection methods that take an enlarged image of pigmentation or the like in a predetermined size of skin with a digital camera. The devices allow for inspecting pigmentation condition of skin tissue through the skin surface to around the dermis with attaching a dermoscope module to a digital camera so as to separately observe respective reflected lights that are reflected on the skin surface and after reaching the dermis. Such digital dermoscopes that have been proposed also include a system that enables to separately observe lights reflected from the skin surface and the inner dermis using a polarization filter.

Dermoscopes have been also used as means of observing pigmentation of skin (e.g., moles) or other lesion such as squamous carcinoma and melanoma to diagnose cancer. In such cases, a dermoscope is configured by attaching a dermoscope module to a camera. In addition, two distinct types of modules, echo gel type module and polarization filter type module, have been employed as dermoscope modules for measuring light reflexes from skin and each has separate characteristics.

An echo gel type module allows for observing the skin surface without using gel, and enables to observe the dermis without producing reflected light on the skin surface by using gel skin surface. On the other hand, a polarization filter module enables to observe reflected light that reaches the dermis by modulating reflected light of the skin surface with a single type of polarization filter without using gel. For example, the specification of U.S. Patent Application Publication No. 2004/0201846 (Patent Document 1) describes a dermoscope for observing skin tissue using a linearly polarized light.

Meanwhile, conventional inspections of pigmentation inside skin have been performed with replacing each module. In conventional cases, a dermoscope must be kept away from the skin upon replacement of the modules, thereby causing positional displacement on the skin to be observed and making the inspection more complicated; this also needs skills for obtaining inspection accuracy.

Furthermore, the conventional dermoscope has required high-intensity light beam for detecting so-called diffuse reflection, which is reflected after passing through the epidermis and reaching the dermal layer, and thus accompanies with an enlarged power supply, an expanded scale of devices, increased weight, and the like, thereby resulting in not good operability. In addition, there has been a problem in that they are not available for medical observation with well distinguishing between direct reflection from the epidermis and diffuse reflection.

CITATION LIST

Patent Literature

[Patent Document 1] The specification of U.S. Patent Application Publication No. 2004/0201846

SUMMARY OF INVENTION

Technical Problem

The present invention was achieved in consideration of the problems belonging to the aforementioned conventional technologies, and the present invention allows for skin tissue inspection in the vicinity of the surface which is comparable with use of the conventional echo gel type module and polarization filter module without taking any inspection module apart from the skin, and also directs to provide an inspection device with improved data accuracy, and a control method, system, light guide and scale of the inspection device.

Solution to Problem

More particularly, the present invention provides an inspection device comprising:
 an imaging device, and
 an inspection module for allowing the imaging device to obtain a tissue image,
 wherein the inspection module comprises:
 an objective lens for focusing reflected light originated from a tissue to the imaging device,
 a plurality of LEDs that surround the optic axis of the objective lens and expose light to the tissue,
 a circular polarization filter comprising a polarization state-regulating parts for exposing the light from the LEDs to the tissue directly or as circularly polarized light, and
 an alignment mechanism for aligning the polarization state-regulating parts with the position of the LEDs.

Advantageous Effects of Invention

The present invention prevents image displacement of a lesion in a skin, a mucosa, an epithelial cell structure, and the like due to displacement of an inspection position by module replacement, and provides highly-accurate and efficient diagnoses. Furthermore, the present invention enables to digitally store a single image as a patient name, an affected part, and a dermoscope image, and provides highly-reliable inspections without misidentification of patients, affected parts, and images.

BRIEF DESCRIPTION OF DRAWINGS

FIG. 2 shows a configuration of a protection member 101, a circular polarization filter 102, and an LED holder 103 of the embodiment, accompanying with the positions of LEDs 103a and polarization state-regulating parts 102a.

FIG. 3 shows an embodiment 200 with positioning LEDs 103a for achieving a direct mode and a polarization mode of the embodiment, and polarization state-regulating parts 102a.

FIG. 12 shows an embodiment of data to be stored in a storage device 1020 by an information-processing device 1010 shown in FIG. 10.

DESCRIPTION OF EMBODIMENTS

Figure 1:
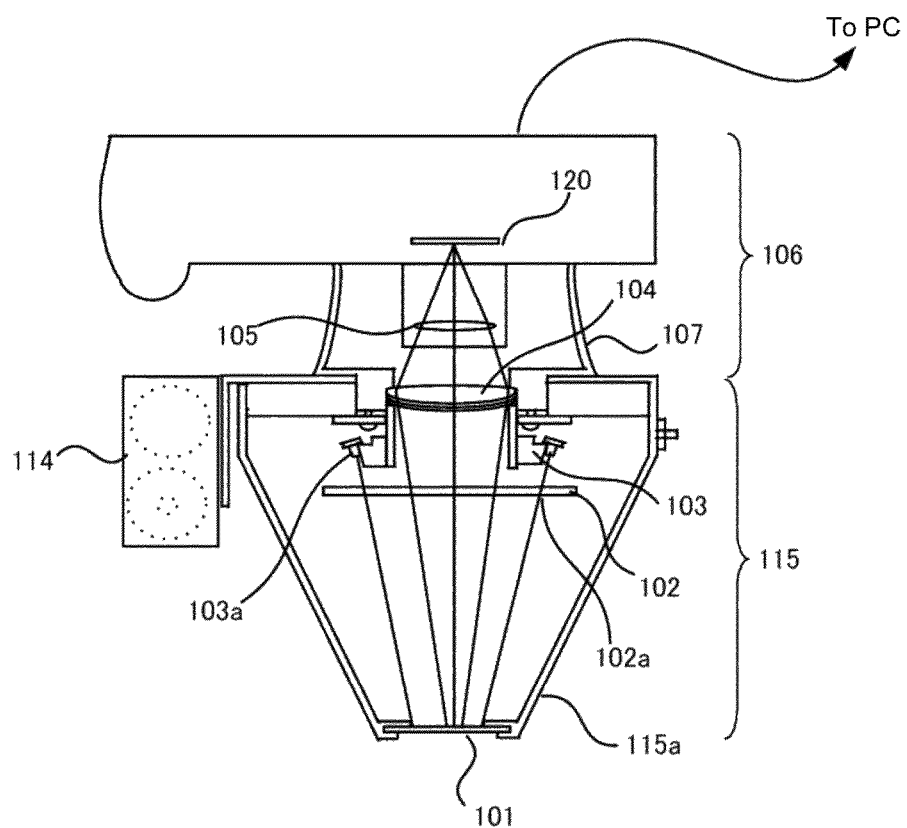
FIG. 1 shows a schematic diagram of an inspection device 100 of the embodiment.

The present invention will now be described with referring to embodiments; however, the present invention shall not be limited to the embodiments below. FIG. 1 shows a schematic diagram of an inspection device 100 of the present embodiment. The inspection device 100 of the present embodiment may be employed as a so-called digital dermoscope, and may include and be configured with an imaging device 106 such as a digital camera, and an inspection module 115. The imaging device 106 and the inspection module 115 may be connected via an adapter 107, and in operation, the imaging device 106 and the inspection module 115 may be integrated and allow to be handled by a physician. The inspection module 115 may comprise a housing 115a formed with an appropriate cone angle, and contain a variety of components in the housing 115a, which provides appropriate stiffness with the inspection module 115 as well as allows for fixation of a battery package 114 and the like.

The imaging device 106 may preferably use a digital camera, but this is not intended to exclude the use of a conventional film camera. The imaging device 106 may be equipped with a lens optics system 105 and an image sensor 120 such as a CCD or CMOS array or a film, and may preferably have a videography function in addition to a still imaging function. In addition, the imaging device 106 may be connected to an information-processing device such as a personal computer by a wired connection such as USB and HDMI or a communication protocol such as Wi-Fi, 3G, 4G, and 5G, and may be allowed to send a still image and/or a video image obtained to the information-processing device to record it remotely.

The inspection module 115 may be constituted to a nearly truncated corn shape, and may include and be configured with an LED holder 103, a circular polarization filter 102 with polarization state-regulating parts 102a, and a protection member 101. The LED holder 103 may be equipped with LEDs 103a and may be supplied direct-current power from a battery (two 1.5 V cells in the embodiment) retained in a battery package 114, and may expose light to a tissue such as a skin, a mucosa, and an epithelial cell structure. Hereinafter the embodiment will generally refer to a part of the human body optically recognizable from outside of the human body, such as a skin, a mucosa, and an epithelial cell structure as a tissue.

The protection member 101 may be formed with glass, clear plastic, or other optically transparent material, and may provide a dustproof function as well as prevent gel or the like, which is applied when inspecting a tissue, from penetrating into the inspection module 115. It may also assist the inspection module 115 to smoothly move on the tissue.

Although the LEDs 103a may be used in any wave length range and luminance already known, white LEDs may preferably be employed in view of observing and imaging flesh color of a tissue such as a skin under the same environment as the normal indoor color temperature. For example, the white LEDs may exemplarily be NSDN510HS-K1 (level b2) manufactured by Nichia Corporation, and those with a color temperature of (X, Y (0, 31, 3.1)) and a Planck color temperature of approximately 6000° C. may be employed.

Meanwhile, in case of no use of white LEDs, RGB colored LEDs may be used, and in such case, the LEDs with peak wave length of 370 nm (violet), 470 nm (blue), 500 nm (yellow), 535 nm (apricot), 570 nm (orange), 630 nm (red), and the like within their wave lengths may be suitably combined to provide a color temperature of approximately 6000° C.

The circular polarization filter 102, in the embodiment, may provide a light isolator function as well as the polarization state-regulating parts 102a. The polarization state-regulating parts 102a in the embodiment may be configured as rounded apertures (with diameters of 5.5 mm-6.5 mm) formed at given intervals in a circumferential direction of the circular polarization filter 102, allowing to provide a mode that exposes light from the LEDs 103a as non-polarized light to a tissue (hereinafter referred to as a direct mode), and a polarization mode that exposes light from the LEDs 103a as circularly polarized light.

The circular polarization filter 102 used in the embodiment may be a general-purpose product for camera optics systems, may have a thickness of 0.28-2.5 mm, and may be made of organic or inorganic material. Furthermore, the polarization state-regulating parts 102a, in the present embodiment, may be described as those configured as rounded apertures that forms rounded openings on the circular polarization filter 102. However, in other embodiments, instead of the rounded apertures, optical materials such as films with no polarization property and circular polarizing materials may also be alternately jointed to constitute a circle or a polygon such as a square, hexagon and an octagon, and the embodiments are not intended to specific structures as long as they provide similar functions.

The light beam from the LEDs 103a, in the present embodiment, may be exposed to a tissue at an angle of approximately 16° 42' against the optical axis. This inclination angle may appropriately suppress irregular reflection from the protection member 101, may be set so as not to generate a gradation of luminance in an observation field of view, and may appropriately arranged depending on the position of the inspection module 115, the optical configuration of the imaging device 106 and other factors.

Reflected light from a tissue may pass through the circular polarization filter 102, and then may be focused to the lens optics system 105 by an objective lens 104 and formed as an image on an image sensor 120 such ad CCD. The image sensor 120 may photoelectrically convert the formed image to generate a digital image. The digital image generated may be displayed on a display part mounted on the imaging device 106 (not shown), and may further be sent to an information-processing device (not shown) so as to be displayed on a display device of the information-processing device asynchronously or synchronously with the display on the imaging device 106.

Figure 2:
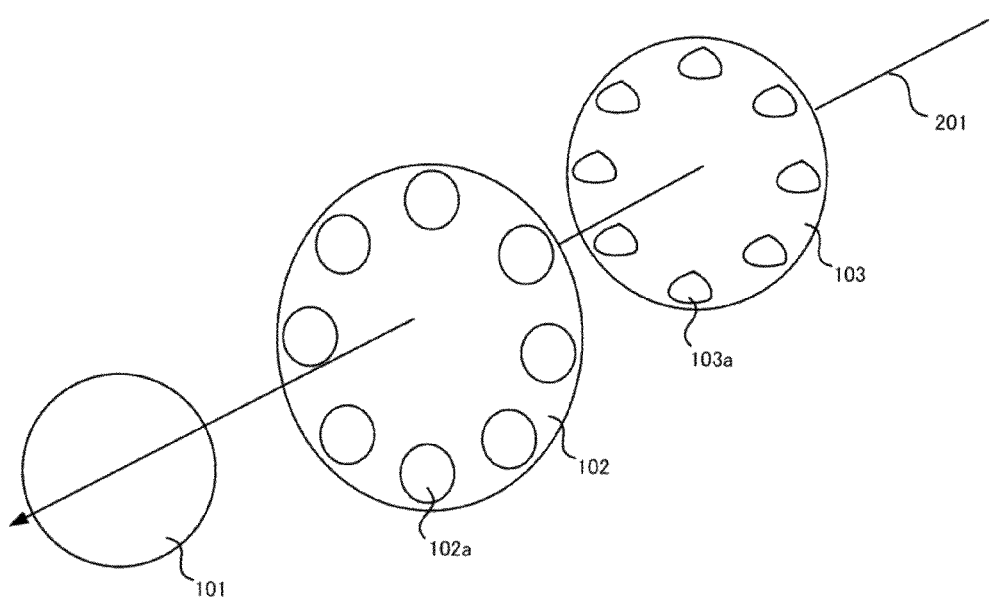

FIG. 2 shows a configuration of the protection member 101, the circular polarization filter 102, and the LED holder 103 of the present embodiment together with positions of the LEDs 103a and the polarization state-regulating parts 102a. The protection member 101, the circular polarization filter 102, and the LED holder 103 may be configured in a concentric fashion with an optical axis 201. The circular polarization filter 102 may be fixed so as to rotate about the optical axis 201, and the LED holder 103 may be fixed to the housing 115a about the optical axis 201. As the circular polarization filter 102 is rotated about the optical axis 201 and aligned with the positions of the LEDs 103a, a direct mode that directly expose light from the LEDs 103a may be set in the embodiment.

On the other hand, as the circular polarization filter 102 is rotated so as to position the LEDs 103a among the polarization state-regulating parts 102a, a polarization mode that exposes circular polarized light to a tissue may be provided. In other word, the embodiment may allow for inspections in a direct mode and polarization mode at the same position without taking the inspection module 115 apart from the tissue.

Figure 3A:
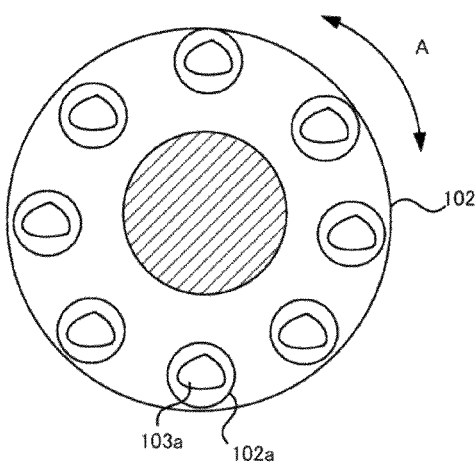
Figure 3B:
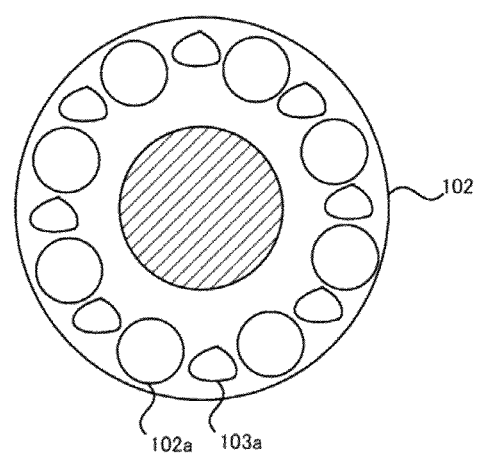

FIG. 3 shows an embodiment 200 of the positions of the LEDs 103a and the polarization state-regulating parts 102a for achieving a direct mode and a polarization mode of the embodiment. FIG. 3(a) shows positions for providing a direct mode, and FIG. 3(b) shows positions for providing a polarization mode. In the direct mode shown in FIG. 3(a), the LEDs 103a and the polarization state-regulating part 102a may be aligned, and a tissue may be directly exposed with light from LED 103a.

Incidentally, the direct mode in the embodiment may be a mode in which light from the LEDs 103a is exposed to a tissue as random mixture of linearly polarized light (non-polarized) due to inner scattering. In FIG. 3(a), the reflected light may pass through a hatched region of the circular polarization filter 102 and may be imaged by the imaging device 106.

On the other hand, the polarization mode shown in FIG. 3(b) may be a mode in which, upon rotation of the LED holder 103 in the direction to the arrowhead A, the positions of the polarization state-regulating parts 102a do not overlap with the LEDs 103a, i.e., light from the LEDs 103a is allowed to pass through the circular polarization filter 102 so as to be exposed to a tissue as circular polarized light. In the embodiment shown in FIG. 3(b), the light from the LEDs 103a may be launched, in a preferable embodiment, into a ¼ wave length plate at $\theta=45°$ or $\theta=-45°$ of ¼ wave length plate by a polarization plate and be exposed to a tissue after being converted to circular polarized light.

In the polarization mode, the circular polarization filter 102 may function as a light isolator and block the directly reflected light from the tissue while transmitting other reflected lights. Therefore, the polarization mode may enable to efficiently block the direct reflection from the tissue, and may permit efficiently to detect the light that passes through the tissue surface to the inside of tissue and reflects after diffusion.

In addition, the illustrative embodiments have been described as that the polarization state-regulating parts 102a may not polarize light from the LEDs 103a, and that other positions may polarize the light from the LEDs 103a. However, in contrast to the above, the polarization state-regulating part 102a may also be configured to polarize light from the LED 103a while other positions polarize the light from the LED 103a, that is to say, for example, a circular polarization filter 102 in which circular polarizing materials with fan shapes are radially formed may be used to function the fan-shaped parts as polarization state-regulating parts 102a. Furthermore, for adjusting a polarization condition, the LED holder 103 may be moved, or in the alternative embodiment, with the LED holder 103 kept fixed, the circular polarization filter may be held in a rotatable filter holder to provide rotation of the filter holder.

Moreover, in the embodiment shown in FIG. 3, the direct mode allows the light from the LEDs 103a to pass through the circular polarization filter 102 once in detection, while the alteration mode allows it to pass through the circular polarization filter 102 once in LED exposure as well as once in detection. Thus, the direct mode will have nearly double detectable amount of light compared to the polarization mode if the LEDs 103a are operated at the same power output. Such difference in the amount of light may also be addressed by adjusting a diaphragm of the imaging device 106.

However, the manipulation for regulating the diaphragm of the imaging device 106 may also require an unnecessary action in medical examination by a physician, and additionally, a positional displacement can accidentally occur in an affected part to be imaged. Thus, it may be preferable in the present embodiment that the polarization mode lights all of the LEDs 103a while the direct mode controls lighting to light the half of the LEDs 103a. The control of lighting may be performed by regulating an electrical connection between the LED holder 103 and the housing 115a depending on rotation of the LED holder 103. Furthermore, a mechanical or software control that provides other similar functions may also be used.

Figures 4A, 4B:
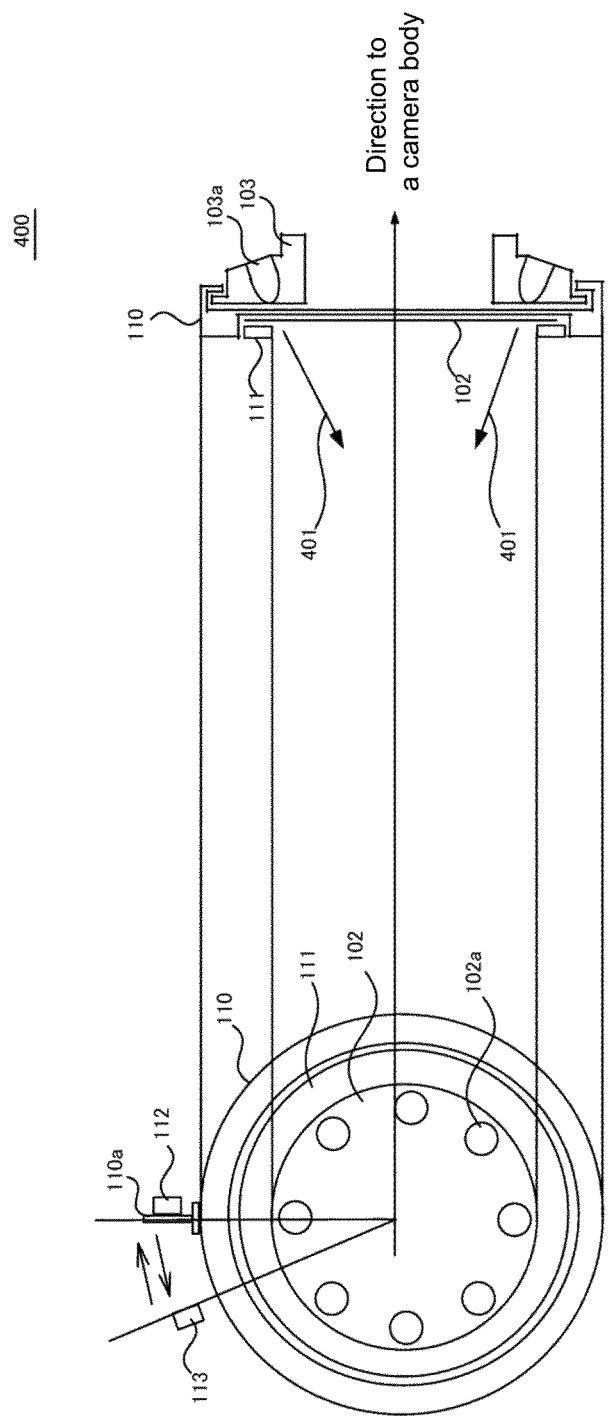
FIG. 4 shows an embodiment of an LED holder 103, a circular polarization filter 102, and a rotation and fastening mechanism of the LED holder 103 of the embodiment.

FIG. 4 shows the LED holder 103, the circular polarization filter 102, and rotation and fastening mechanism of the LED holder 103 of the present embodiment. FIG. 4(a) shows a plane view, and FIG. 4(b) shows a side view. As shown in FIG. 4(a), a knob 110a made of magnetic material may be formed in a filter-holding part 110. Furthermore, the housing 115a of the inspection module 115 has magnets 112 and 113 fixed thereto, which may alterably fix a position of the circular polarization filter 102 relative to the LEDs 103a.

A configuration of the circular polarization filter 102 and the LED holder 103 will be now described with referring to FIG. 4(b). The circular polarization filter 102 may be held with a filter-holding member 111 to the filter-holding part 110 rotatably about an optic axis. On the other hand, the LED holder 103 may be held with the housing 115a. Thus, a physician that performs an inspection, may enable to alternatively displace the position of the polarization state-regulating parts 102a to the position overlapped with the LEDs 103a or the position displaced therefrom by putting his/her finger on the knob 110a and rotating the circular polarization filter 102.

The LED holder 103 may also be held inclined toward the optical axis so as to expose light to a tissue at an angle of approximately 16° 45', and expose lights 401 and 402 from the LEDs 103a to the tissue. Additionally, in the present embodiment, the distance between the LEDs 103a and the protection member 101 may be approximately 60 mm, although such distance may be altered depending on the configuration of a particular device.

Figure 5:
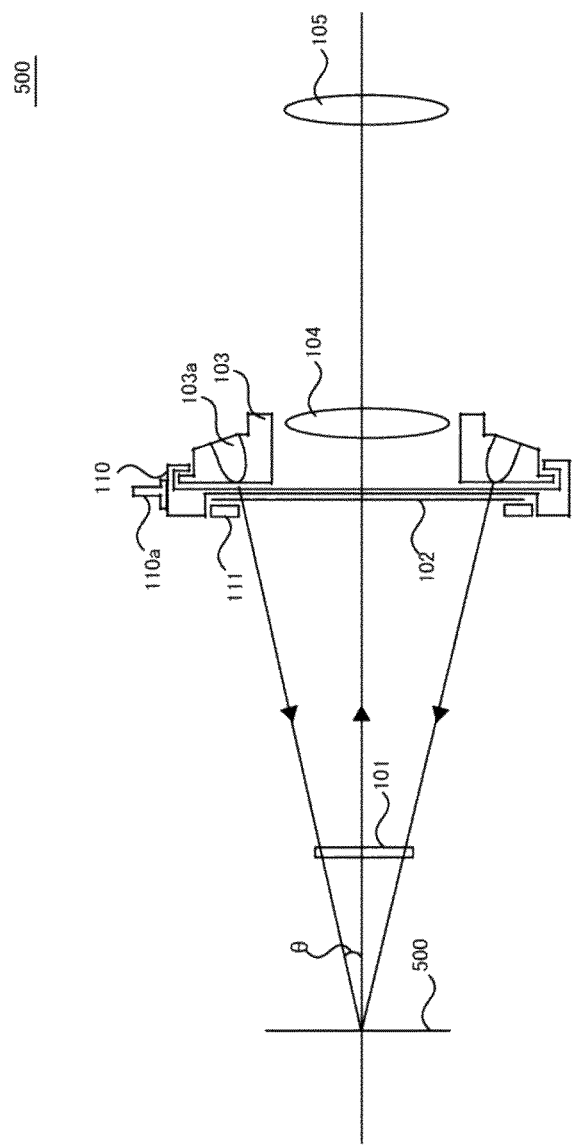
FIG. 5 shows a pattern diagram illustrating an exposing optics system with the LEDs 103a of the embodiment.

FIG. 5 shows a schematic diagram illustrating an exposure optics system with the LEDs 103a of the present embodiment. The LEDs 103a may expose unpolarized light or circular polarized light to a tissue 500. The light after passing through the protection member 101 may be exposed to the tissue 500 at an exposure angle of approximately 16° 45' as mentioned above, and then reflected at the tissue 500 to generate reflected light.

The reflected light may pass through the circular polarization filter 102 both in the direct mode and polarization mode, and then reach an objective lens 104. The reflected light that reaches the objective lens 104 may go to a lens optics system 105 in the imaging device 106 by the objective lens 104 to focus image on an image sensor 120. The knob 110a may be formed on the filter-holding part 110, thereby making the relative positioning adjustably between the polarization state-regulating part 102a and the LEDs 103a.

Figure 6:
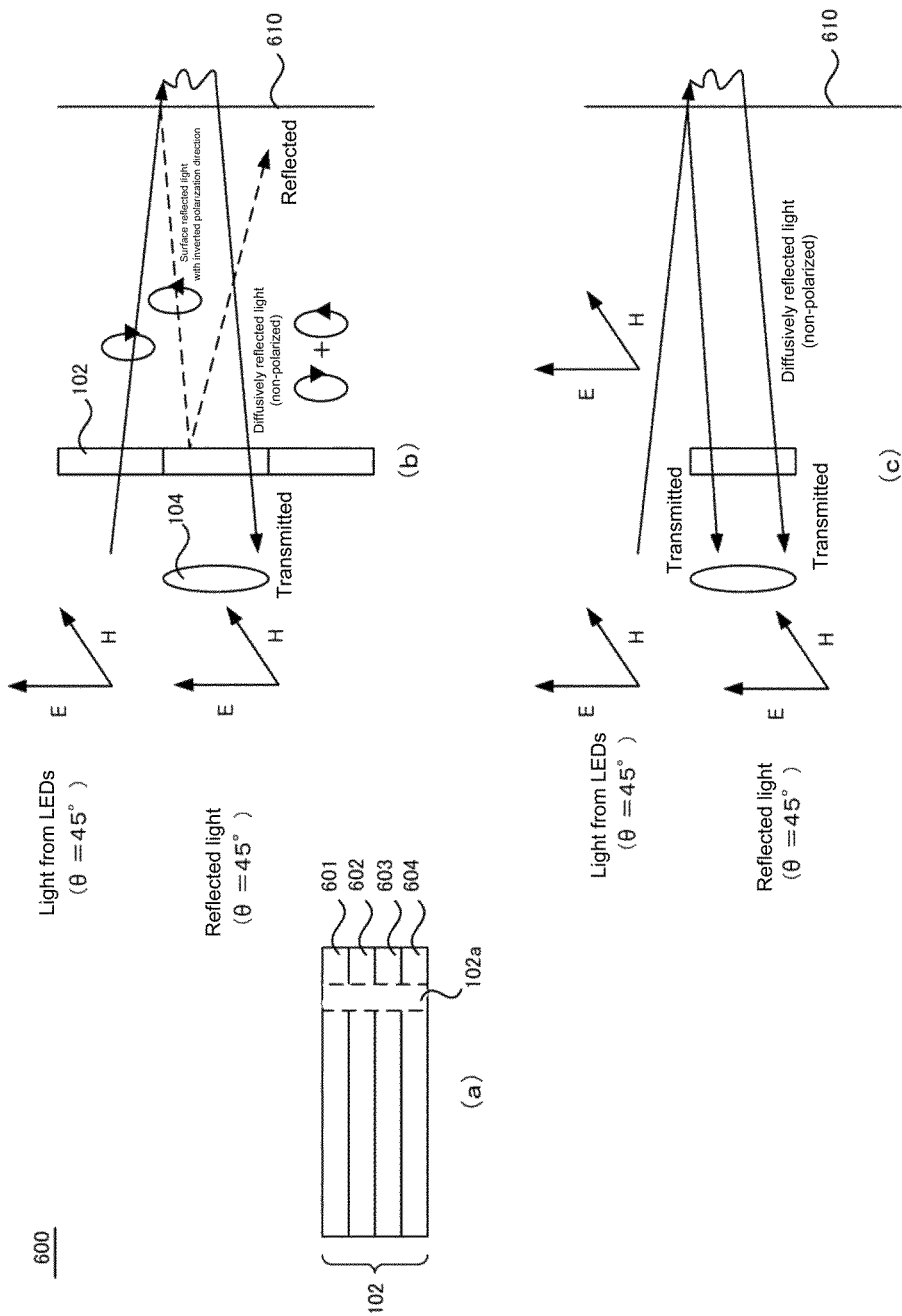
FIG. 6 illustrates light detection mechanisms in a direct mode and a polarization mode in the embodiment.

FIG. 6 illustrates a light detection mechanism in the direct mode and the polarization mode of in the present embodiment. FIG. 6(a) shows an exemplary configuration of the circular polarization filter 102, FIG. 6(b) shows a light detection mechanism in the polarization mode, and FIG. 6(c) shows a light detection mechanism in the direct mode.

The circular polarization filter 102 used in the present embodiment may be a commercially-available product for a camera, and in the present embodiment, formation of the polarization state-regulating parts 102a in a commercially-available circular polarization filter 102 may lead to a configuration to permit to alternate between the polarization mode and the direct mode by a rotating operation without taking the inspection device 100 away from the tissue. The circular polarization filter 102 may generally include and be configured with a polarizing plate 602 and a ¼ wave length plate 603 protected with a protection film 601 and 604. Light from the LEDs 103a may be launched from the upper side of the paper to the circular polarization filter 102.

In unpolarized light from the LEDs 103a, light in the direction of an electric field vector E, e.g., with θ=45°, relative to the optic axis of the ¼ wave length plate 603 may be polarized with a polarizing plate 602, and may pass through a ¼ wave length plate 603. The ¼ wave length plate 603 may generate a phase shift of the electric field vector E of the linearly polarized light by ¼ wave length ($\pi/2$) to convert into circular polarized light, and then may transmit it to the bottom side in the drawing.

A light detection mechanism of the present embodiment will be detailed below with referring to FIG. 6(b) and FIG. 6(c). In detection of reflected light, the reflected light may be launched from the bottom side of the paper into the circular polarization filter 102, and transmit toward the upper of the paper. FIG. 6(b) shows a light detection mechanism of the polarization mode in the present embodiment. As light from the LEDs 103a is launched into the circular polarization filter 102, the light in the predetermined polarization direction that has an electric field vector E, e.g., with θ=45° relative to the optic axis of the ¼ wave length plate 603, may be selectively transmitted with the polarizing plate 602, may pass through the ¼ wave length plate 603, and may be exposed to a tissue 610 as circularly polarized light.

The tissue 610 may reflect light on its surface, but most of the exposed light may enter into the epidermis, and generate diffuse reflection scattered in the tissue. At the time, in the light directly reflected at the surface of the tissue 610, the direction of the circular polarized light may be inverted, for example, the right-handed circularly polarized light may be reflected as the left-handed circularly polarized light as illustrated. This reflected light may be launched into a ¼ wave length plate in the circular polarization filter 102.

In this case, the light beam that passes through the ¼ wave length plate 603 may be converted to linearly polarized light with θ=−45°, and thus may be reflected and not detected due to a function of the polarization plate 602 in the circular polarization filter 102. In other words, the circular polarization filter 102 may function as a light isolator for directly reflected light in the embodiment.

The right-handed circularly polarized light that passes thorough inside of the tissue may reach the circular polarization filter 102 as an unpolarized state with mixture of right-handed circularly (elliptically) polarized light and left-handed circularly (elliptically) polarized light due to irregular reflection. The ¼ wave length plate 603 may, in the reflected light in such state, convert both of the right-handed circularly polarized light and right-handed elliptically polarized light into linearly polarized light regardless of phase φ relative to the direction of the light. The polarization plate 602 in the circular polarization filter 102 may transmit both right-handed circularly polarized light and right-handed elliptically polarized light, as long as they may be converted to linearly polarized light with θ=45° relative to the optic axis by the ¼ wave length plate 603.

Therefore, the polarization mode may efficiently reduce the impact of the surface reflection, and allow for an efficient measurement of reflection from inside of the tissue. In addition, unlike a linearly polarized light filter in a crossed arrangement, the ¼ wave length plate 603 may permit even reflected light of elliptically polarized light, in spite of resulting in difference in transmittance, to pass through the circular polarization filter 102. Thus, the intensity of reflected light in the polarization mode may be much improved compared to the use of the crossed arrangement up to approximately 1000 fold. This may enable the inspection device 100 used in the embodiment to operate with low illuminance, i.e., relatively low electric power, and may provide miniaturized device.

On the other hand, in the direct mode, the light from LEDs 103a may be exposed to the tissue 610 with substantially keeping unpolarized. In such case, even if the reflected light from the tissue surface reflects at this case, the direction of the electric field vector E may be substantially maintained, and the surface reflected light may also be allowed to pass through the ¼ wave length plate 603 and the polarizing plate 602. Meanwhile, since the reflected lights reflected inside the tissue may have been reflected with the substantially unpolarized condition due to irregular reflection inside the tissue, the ¼ wave length plate 603 and the polarizing plate 602 may pass the polarized reflected light which is able to pass thorough the polarizing plate 602 placed at θ=45°, among the reflected lights.

In other words, the direct mode may pass both surface reflection and diffuse reflection through the circular polarization filter 102 without any substantial isolation. Incidentally, the reflected light from direct reflection may be reflected toward the objective lens 104 much more efficiently than that from diffuse reflection. By contrast, the diffuse reflection may be dispersed in its direction due to irregular reflection inside the epidermis and may decrease in reflectance itself toward the objective lens 104. Given such reflectance, it is considered that the direct mode may mainly provide observation of direct reflection.

That is to say, the direct mode may facilitate better detection of direct reflection, while the polarization mode may provide more emphatic observation of diffuse reflection. Without wishing the embodiment to be bound to any specific theory, it is inferred that the light detection mechanism illustrated in FIG. 6 may be a factor that provides good detection of diffuse reflection in the polarization mode in the present embodiment.

Figure 7:
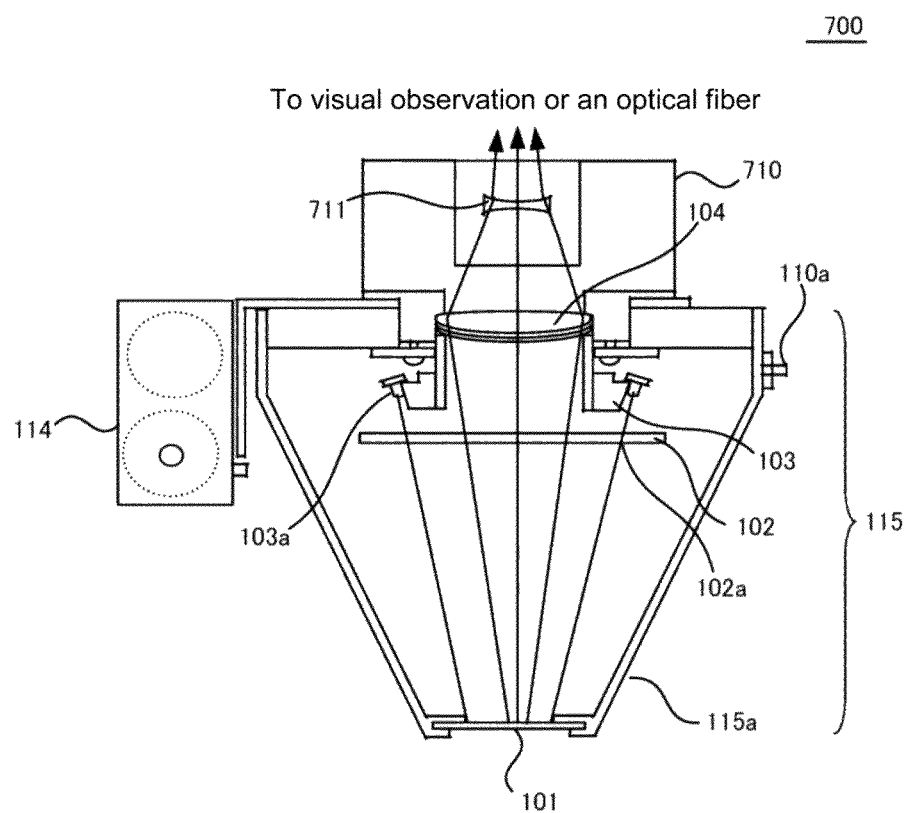
FIG. 7 illustrates a second embodiment of an inspection module 115 of the embodiment.

FIG. 7 shows a second embodiment of the inspection module 115 of the embodiment. The second embodiment may be configured with separating the imaging device 106 from the inspection module 115, and may permit a physician to manually operate a more lightweight inspection module 115 to perform inspection. As a result, it may be possible to reduce elaboration upon operation for an inspector such as a physician.

The inspection module 115 of the second embodiment may be one in which an eyepiece part 710 is further added to the inspection module 115 shown in FIG. 1, and may form the light focused at the objective lens 104 into nearly parallel light beams at a concave lens 711, thereby allowing for direct observation by a physician. In a further embodiment, the configuration may be one in which an optical fiber is connected to the eyepiece part 710, an image is sent to the imaging device 106 remotely installed, and then the image from the inspection module 115 is confirmed on a liquid crystal display device on the body of the imaging device 106 or on a display device in an information-processing device by a physician. Thus, the embodiment shown in FIG. 7 may enable an inspector such as a physician to pay attention for inspections without forcing to take an unnatural posture.

The embodiment shown in FIG. 7 may allow to reduce manual operation to the inspection device 100 only to the inspection module 115, and may improve operability as well as may permit to confirm the images independently of the geometric position of the imaging device 106, thereby providing improvement of handleability.

Figure 8:
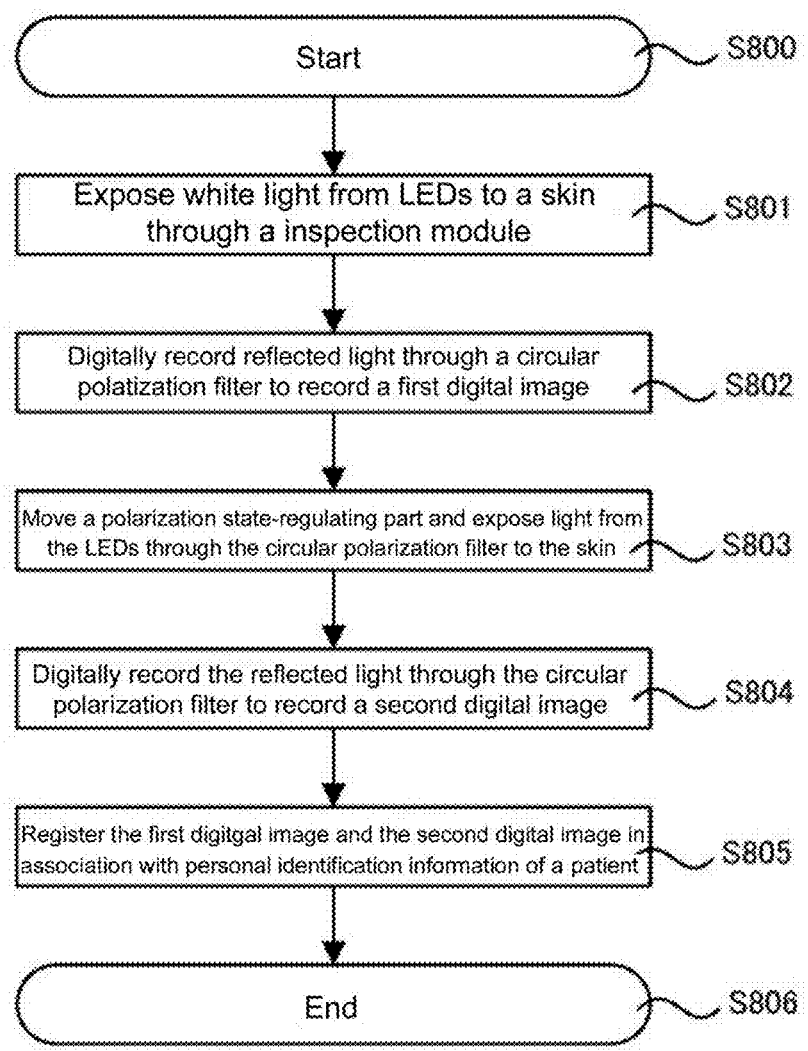
FIG. 8 shows a flow chart for performing a control method of the inspection device 100 for tissue inspection of the embodiment.

FIG. 8 shows a flow chart of a control method of the inspection device 100 for tissue inspections of the embodiment. A process of FIG. 8 may start at step S800, and may directly expose light from the LEDs 103a through the inspection module 115 to a tissue at step S801. At step S802, reflected light may be digitally recorded through a circular polarization filter to record a first digital image. At step S803, a polarization state-regulating part may be rotated, and then light from the LEDs 103a may be exposed through the circular polarization filter 102 to the tissue.

At step S804, the reflected light may be digitally recorded through the circular polarization filter 102 to form a second digital image. At step S805, the first digital image and the second digital image may be registered in association with personal identification information of a patient. In such case, the registration may be performed in the imaging device 106 itself, or may be directly recorded in an information-processing device connected to the imaging device 106. The control method in FIG. 8 may then finish at step S806.

In the embodiment shown in FIG. 8, observation by a physician or the like may be performed on a liquid crystal display equipped on the imaging device 106, and a physician may explain about a taken image on the information-processing device for a patient after the inspection.

Figure 9:
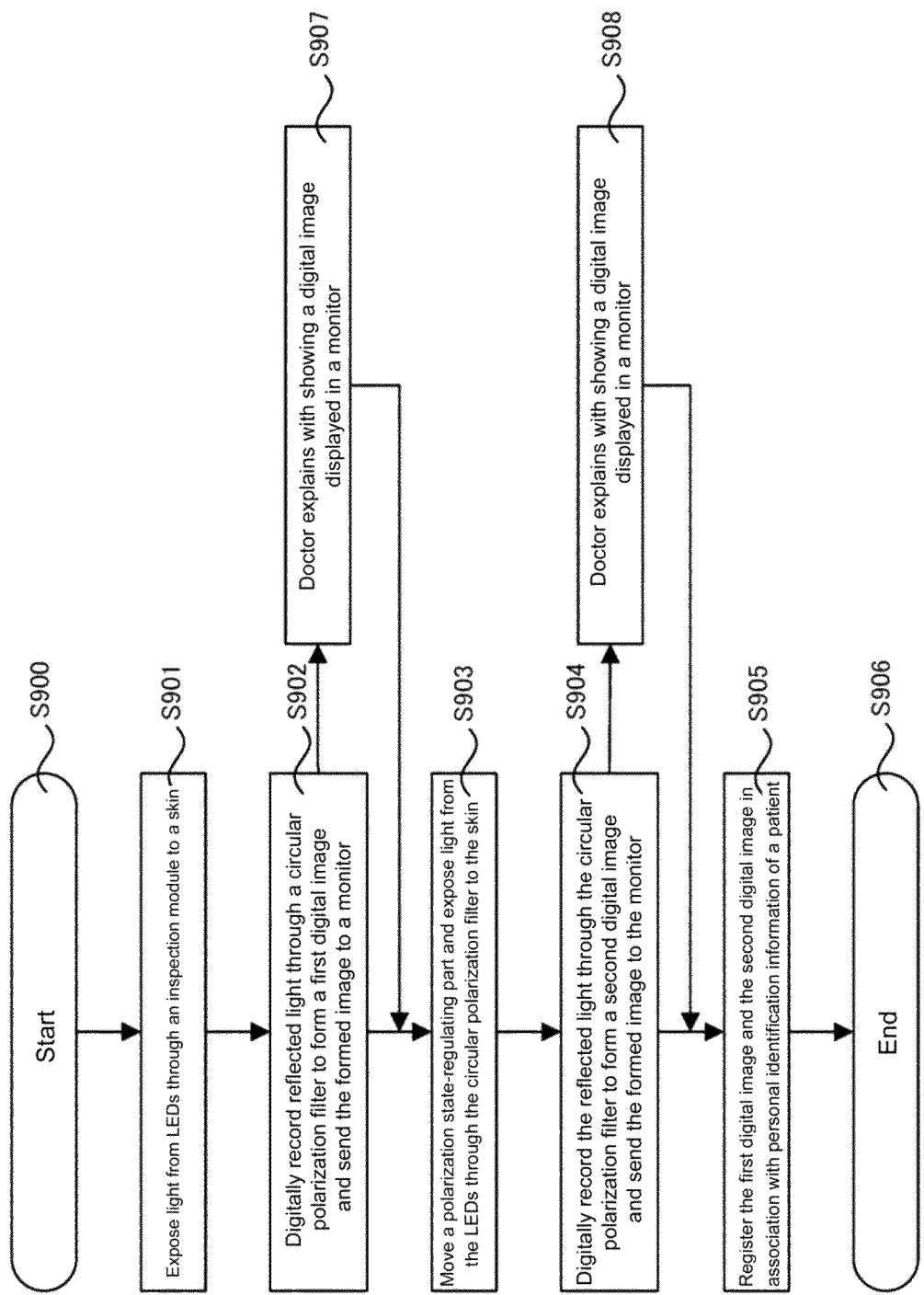
FIG. 9 shows a flow chart for performing a control method of a second embodiment of the inspection device 100 for skin inspection of the embodiment.

FIG. 9 shows a flow chart of a control method of the second embodiment of the inspection device 100 for tissue inspections. A process of FIG. 9 may start at step S900, and may directly expose light from the LEDs 103a through the inspection module 115 to a tissue at step S901. At step S902, reflected light may be digitally recorded through the circular polarization filter 102 to record a first digital image. At the same time, the imaging device 106 may also send the taken image to an information-processing device. At step S807, the image may be displayed on a monitor in the information-processing device, thereby allowing for explanation by a physician simultaneously with the ongoing inspection.

Furthermore, at step S904, the light from the LEDs 103a may be exposed through the circular polarization filter 102 to the tissue. At step S904, the reflected light may be digitally recorded through the circular polarization filter 102 to form a second digital image. At the same time, the imaging device 106 may also send the taken image to the information-processing device. At step S908, the image may be displayed on a monitor in the information-processing device, thereby allowing for explanation by a physician simultaneously with the ongoing inspection.

Then, at step S905, the first digital image and the second digital image may be registered in association with personal identification information of a patient. In such case, the registration may be performed in the imaging device 106 itself, or may be directly recorded in an information-processing device connected to the imaging device 106, as similar with the first embodiment. The control method in FIG. 9 may then finish at step S906.

The second embodiment may allow a physician to perform inspection as well as to take informed consent from a patient with showing a display device in an information-processing device, and thus may provide medical care with higher patient satisfaction. In addition, a physician may enable to perform inspection apart from the spatial position of the imaging device 106 using a more enlarged image, thereby also providing improvement of inspection quality.

Figure 10:
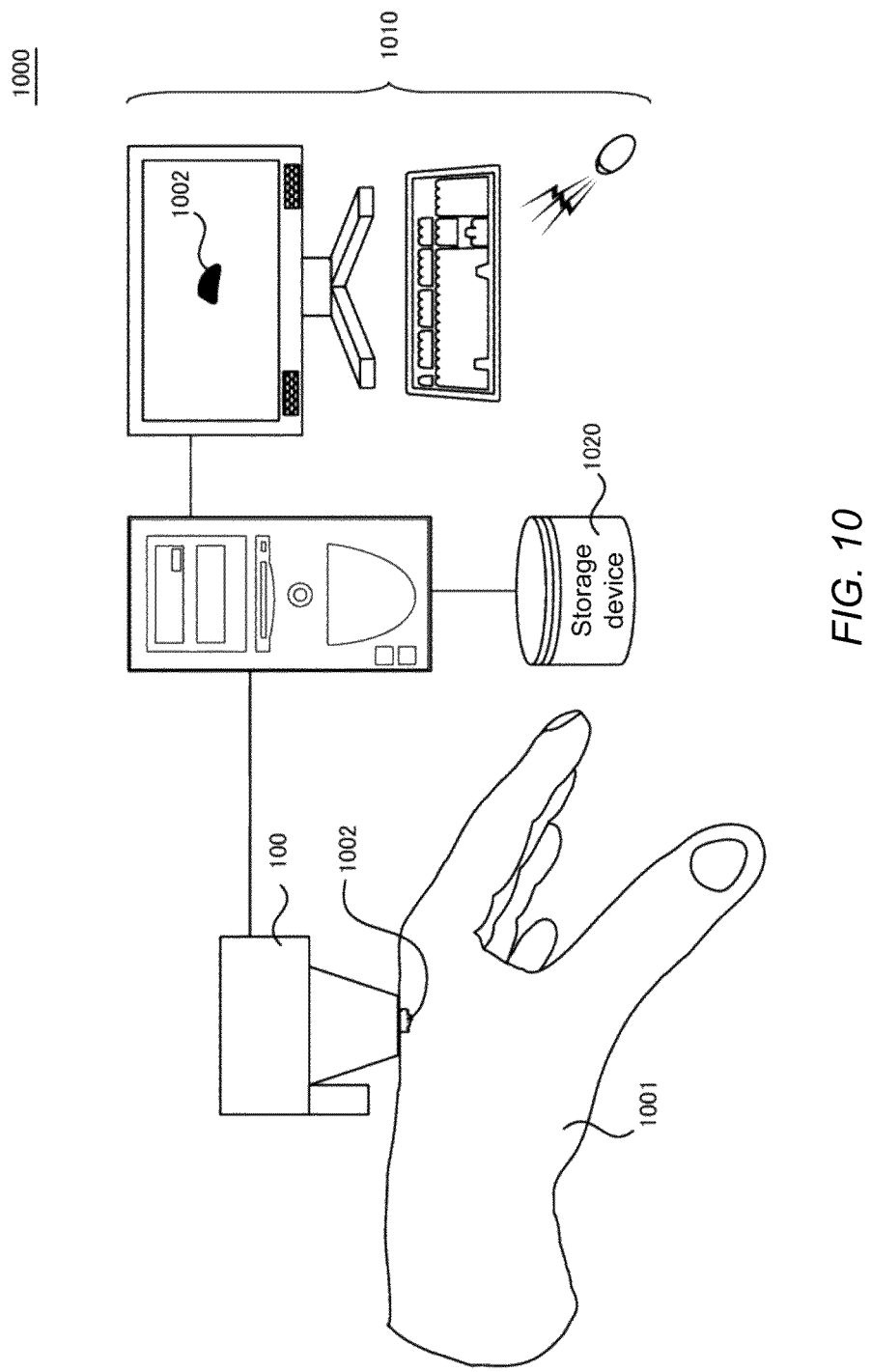
FIG. 10 shows an embodiment of an inspection system 1000 using the inspection device 100 of the embodiment.

FIG. 10 shows an embodiment of an inspection system 1000 using the inspection device 100 of the embodiment. The inspection system 1000 of the embodiment may include and be configured with the inspection device 100 of the embodiment, and an information-processing device 1010 containing factors such as a display device, a keyboard, and a mouse. The information-processing device 1010 may include and be configured with CPU for executing a program of the embodiment, a memory, and a storage device 1020, and may function the information-processing device so as to execute each step of the embodiment.

Incidentally, the connection between the inspection device 100 and the information-processing device 1010 may be USB connection or Wi-Fi connection, or may otherwise use wireless LAN connection via IEEE802.11x, as mentioned above. In addition, the connection between the inspection device 100 and the information-processing device 1010 may be appropriately modified depending on user needs.

The inspection device 100 may contact with an affected part 1002 of a patient 1001, the image thereof is, in an illustrative embodiment, displayed on the imaging device 106 itself as well as on a display device in the information-processing device. The image of the affected part 1002 displayed on the display device may be enlarged more than that on a liquid crystal display equipped in the imaging device 106, thereby providing more clear and highly accurate inspections.

The information-processing device 1010 may also have the storage device 1020 such as a hard disk, and may store digital images taken in the direct mode and the polarization mode with linking them to personal information, for example, in database format. According to the embodiment, images plurally generated for at least one patient 1001 in the direct mode and the polarization mode may be linked to personal identification information of the patient 1001 and may be recorded as a set of operations, thereby efficiently preventing mistake such as misidentification of diagnosis contents.

As the results, the embodiment may permit attention of a physician not to be devoted for operating an information-processing device but to be directed for diagnosis, thereby providing further improvement of inspection quality.

Figure 11:
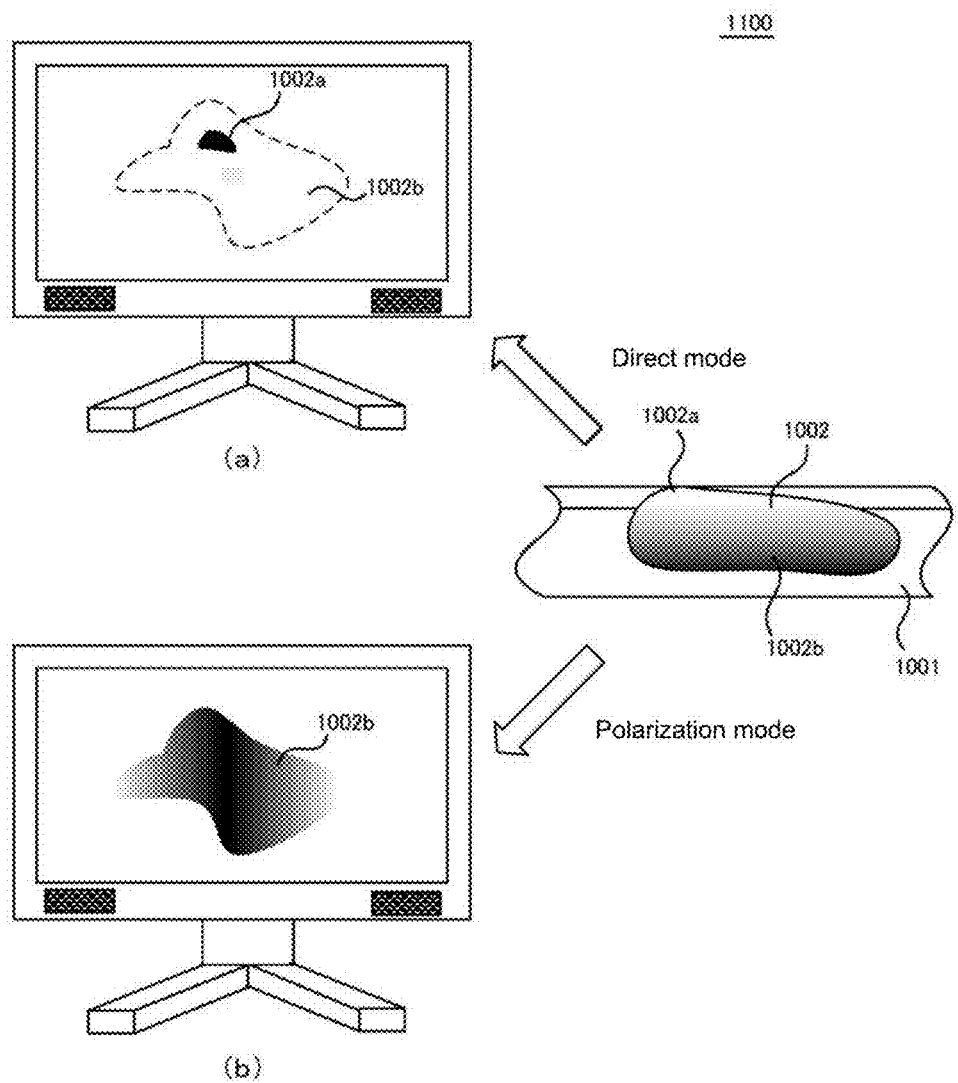
FIG. 11 shows a schematic diagram illustrating a difference of affected part image between a direct mode and a polarization mode according to the embodiment.

FIG. 11 shows a schematic diagram illustrating a difference of affected part images of the direct mode and the polarization mode of the embodiment. As shown in FIG. 11, a skin tissue in the patient 1001 may contain a dermis tissue inside epidermis other than a skin surface, which may constitute a tissue. In this structure, a skin disease may possibly not only spread the epidermis part but also reach the subsequent dermis tissue therebelow. Thus, in superficial observation, even if the affected part 1002 is not visible in a surface observation, as indicated as a site 1002a, the affected part 1002 may occasionally infiltrate deep inside to the dermis tissue, as indicated as a site 1002b.

Observation in the direct mode may not provide sufficient separation of reflections from the juxtaepidermal site 1002a and the inner site 1002b, and may also allow direct reflection from the epidermis to be detected with higher intensity, and thus may not be suitable for observing the diffuse reflection that reaches to dermis with sufficient S/N ratio. Accordingly, although an image involving the epidermal site 1002a may be clearly observed, the intradermal site 100b may only be observed with low contrast as shown in FIG. 11(a) or even may not be observed, and furthermore may not be clearly diagnosed for its spread, form, coloring, and erosion and/or exudation associated with cell wall infiltration.

By contrast, in observation of the affected part 1002 in the polarization mode, direct reflection with stronger intensity may be cut off by light isolator function of the circular polarization filter 102 as described using FIG. 6, and reflected light from the site inside the tissue 1002b may be detected. Therefore, an affected part image to be displayed on a display device will clearly show the site inside the tissue 1002b, thereby providing further improvement of inspection accuracy.

Additionally, in the embodiment, luminance of the LEDs 103a may also be adjusted so as to regulate background illuminance between the direct mode and the polarization mode to make comparative judgement under nearly similar brightness. The adjustment of the luminance may employ, for example, a configuration in which: the knob 110a may be coupled to a selector switch, and the direct mode may have e.g., the half of the LEDs 103a lighting so as to provide low amount of light, while the polarization mode may light all.

In a further embodiment, the inspection module 115 may also be equipped with a volume for adjusting luminance of the LEDs 103a so that background luminance may be comparable depending on characteristics of the specific inspection module 115. Moreover, any previously known method available for adjusting luminance of the LEDs 103a may be used.

Then, in the present embodiment, the position of the inspection module 115 may remain unchanged between the direct mode and the polarization mode, thereby allowing to judge the level of infiltration in the affected part without consideration for positional displacement, reducing inspection burden of a physician while providing more highly accurate diagnosis.

FIG. 12 shows an embodiment of data to be stored in the storage device 1020 by the information-processing device 1010 shown in FIG. 10. In the present embodiment, image data may be generated as a pair from the direct mode and the polarization mode, such as data 1, data 2 . . . in time sequence. These data may also be stored in association with personal identification information of the patient 1001 as a set at the end of diagnosis without fail. Therefore, a physician will not register data with incorrect association, thereby allowing to prevent misidentification of results and the like. Moreover, imaging dates may also be registered with accurate association, thereby also permitting to improve continuous diagnostic accuracy.

Figure 13:
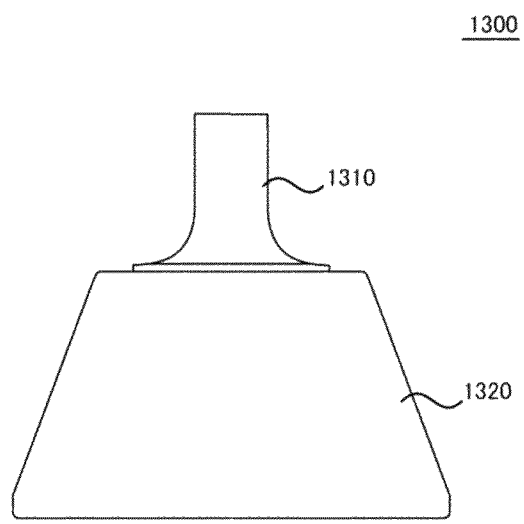
FIG. 13 shows a side view of a light guide 1300 of the embodiment.

A light guide 1300 mounted on the inspection device 100 of the present embodiment will be described below with use of FIG. 13-FIG. 15. FIG. 13 shows a side view of the light guide 1300 of the present embodiment. The light guide 1300 of the present embodiment may be mounted on the tip of the inspection module 115 of the inspection device 100 to expose LED light to a narrow affected part region, and may lead reflected light reflected from a narrow region of the tissue affected part to of an objective lens of a camera.

Figure 14:
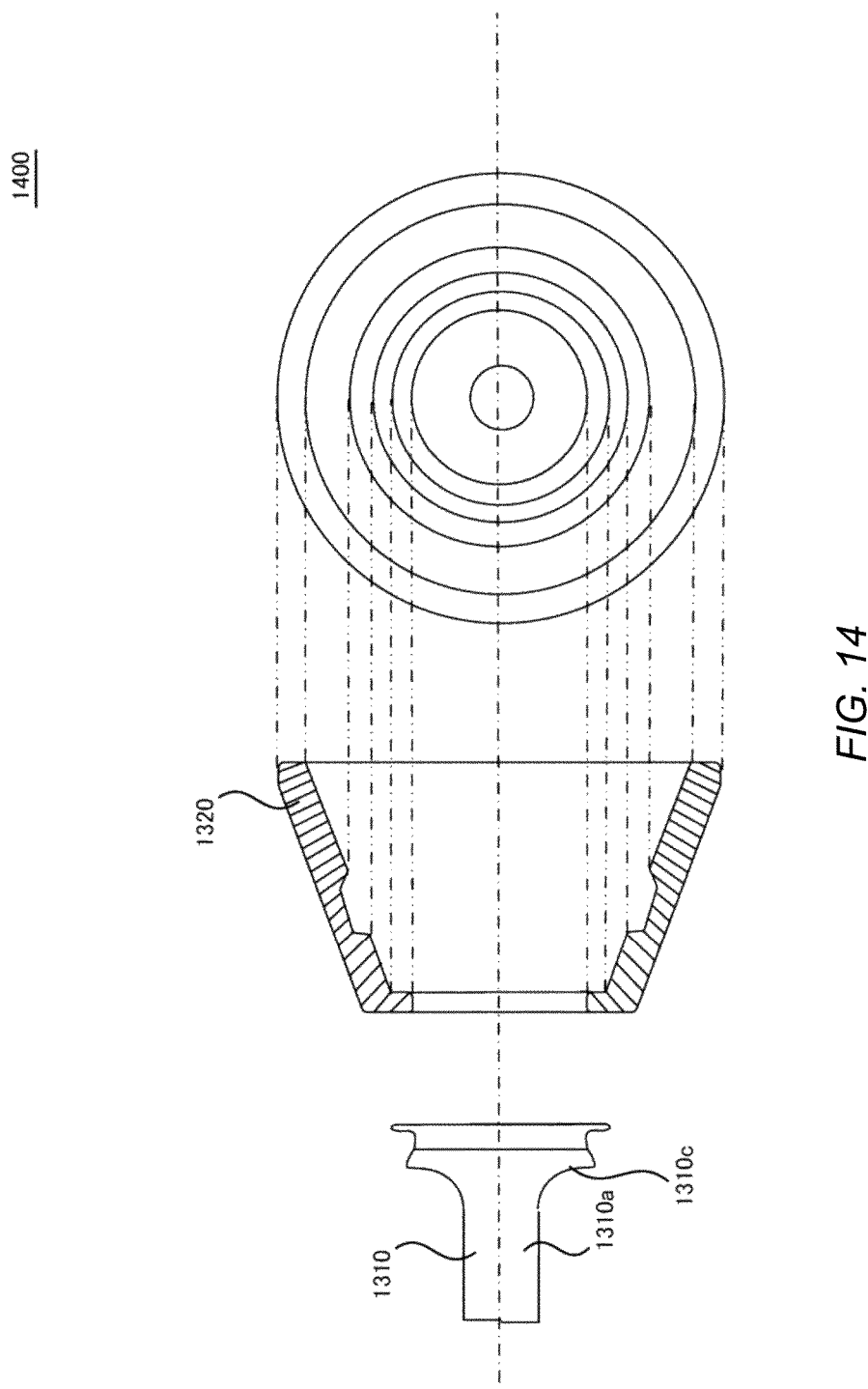
FIG. 14 depicts an exploded view showing a configuration of the light guide 1300 of the embodiment.

FIG. 14 shows an exploded view illustrating the light guide 1300 of the embodiment. It may be configured with a light-guide member 1310 and an adapter 1320. The light-guide member 1310 may be formed for example, by cutting out optical grade resin material such as polycarbonate resin or PMMA, and may comprise a light guiding part 1310a that extends about the center axis, and a base part 1310c that is contiguous to the light guiding part 1310a for holding the light-guide member 1310 to the holder 1320. The light guiding part 1310a may have optical grade flat surfaces on its tip surface and on a base part surface of the base part 1310c so as to avoid scattering as well as undesired attenuation of transmitted light.

The tip of the light guiding part 1310a may contact with a region such as a affected tissue part and expose light exposed through the inspection module 115 to the affected part. The light guiding part 1310a may also lead reflected light from the tissue to the objective part of the camera through the polarization filter-holding part.

Moreover, the outer face of the light guiding part 1310a and the outer face of the base part 1310c may be finished with frosted glass so as to avoid entry of stray light from outside, and may constituted so as to prevent light beam from outside except for the affected part from entering into the light guiding part 1310a.

An adapter 1320 may be formed as a nearly hollow truncated corn, and the cross-section thereof is shown in FIG. 14. The adapter 1320 may have the inner shape formed to fit the outer shape of the inspection module 115 and may be detachably fastened to the inspection module 115 with frictional force as well as contractile force at the tip of the inspection module.

FIG. 14 also shows an inner structure of the adapter 1320 and a structure of the bottom surface in a side attached with the inspection module 115 in association with the inner shape of the holder 1320. The adapter 1320 may be formed with a soft material such as white silicone resin and may hold the light-guide member 1310 at its one end while being mounted on the tip of the truncated corn-shaped inspection module 115 at the other end, thereby allowing to detachably hold the light-guide member 1310 with frictional resistance of the material constituting the adapter 1320.

The inner surface of the adapter 1320 may have a thinner part circumferentially formed for reducing frictional resistance at insertion/removal. Furthermore, the end of the adapter 1320 may have an opening formed for holding the base part 1310c of the light-guide member 1310, thereby holding the light-guide member 1310 with elastic force of silicone resin forming the adapter 1320.

On the other hand, the larger diameter end of the adapter 1320 may have a tapered shape attachable to the tip of the truncated corn on the inspection module 115, thereby holding the base part 1310c of the light-guide member 1310 to the camera with fastening the base part 1310c to be attached closely to the tip part of the polarization filter-holding part.

A configuration of the light guide 1300 of the present embodiment will be described with use of FIG. 14. The base part 1310c of the light-guide member 1310 may be inserted into an opening part formed at the smaller diameter side of the adapter 1320 to hold a notch formed in the base part 1310c with the edge of the opening part at the smaller diameter side of the adapter 1320, thereby forming the light guide 1300 for a camera. The opening at the larger diameter side of the adapter 1320 may be fixed at the tip of the inspection module 115 with frictional force.

In the embodiment, the light guiding part 1310a centering on the light-guide member 1310 may be optically transparent, thereby transmit light with little optical loss to the base. On the other hand, frosted glass finish may be provided from the outer face of the light guiding part 1310a to the base part 1310c of the light-guide member 1310 so as to avoid entry of stray light from the surroundings into the light guiding part 1310a. Thus, this may enable to prevent light beam from outside from entering into the light guiding part 1310a of the light-guide member 1310. Moreover, the inside of the light guiding part 1310a toward the base part 1310c may be optically transparent, thereby allowing to efficiently expose LED light through the light-guide member 1310 and to further lead the reflected light to the imaging device 106.

Figure 15:
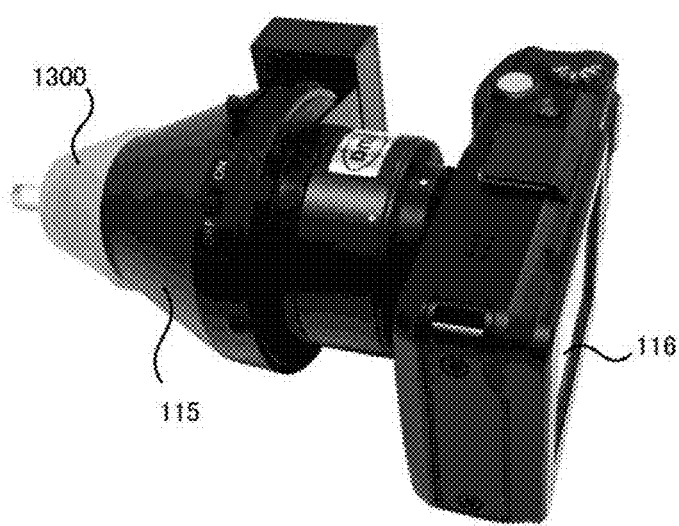
FIG. 15 shows a use aspect with a light guide 1330 of the embodiment mounted on the inspection module 115.

FIG. 15 shows a use aspect of a light guide 1330 when the light guide 1330 of the present invention is put on the inspection module 115. The light guide 1330 may be used by mounting on the tip of the inspection module 115 attached to the imaging device 116. In use of light guide 1330, the light guiding part 1310a at the tip of the light guide 1330 may be disposed closely so as to contact with a narrow affected part such as a tissue between the fingers, under the arm, on the sole of the foot, inside the oral cavity, and inside the acoustic pore. The imaging device 116 may allow to take an image of the affected part in a tissue with eliminating stray light from outside.

A scale 1600 of the present embodiment will be described with using FIG. 16 and FIG. 17. The scale 1600 of the present embodiment may be mounted on the tip of the inspection module 115, and may allow the imaging device 116 to take a predetermined dimension such as 1 mm scales with an affected part. Thus, a physician who images an affected part with the imaging device 116 may directly know the size and area of lesion of the affected part using the dimension of scale from the taken image.

The scale 1600 of the present embodiment will be detailed below with use of FIG. 16. The scale 1600 of the present embodiment may have a structure with a scale member 1610 inserted into the adapter 1320, thereby holding the scale 1610 on the upside level of the adapter 1320. The scale member 1610 may be processed by cutting out plastic material which is optically graded on the top surface and the bottom surface, and may have the bottom surface with, for example, scales with 1 mm intervals by laser engraving. The bottom surface may be formed so as to have a diameter larger than the top surface, thereby providing a shape in which the concave part between the top surface and the bottom surface may be inserted into an opening formed on the upper side of the holder to allow the adapter 1320 to hold the scale 1610.

In the scale member 1610, the bottom surface of the scale member 1610 may have scales 1610a with predetermined intervals such as 1 mm engraved with surrounding the field of view, and the scales 1610a may be modified in color or transparency relative to regions other than scales 1610a so as to provide optical visibility. The color may be, for example, black, but may also be white so long as the transmittance may be modified so as to provide optical recognition.

Figure 16:
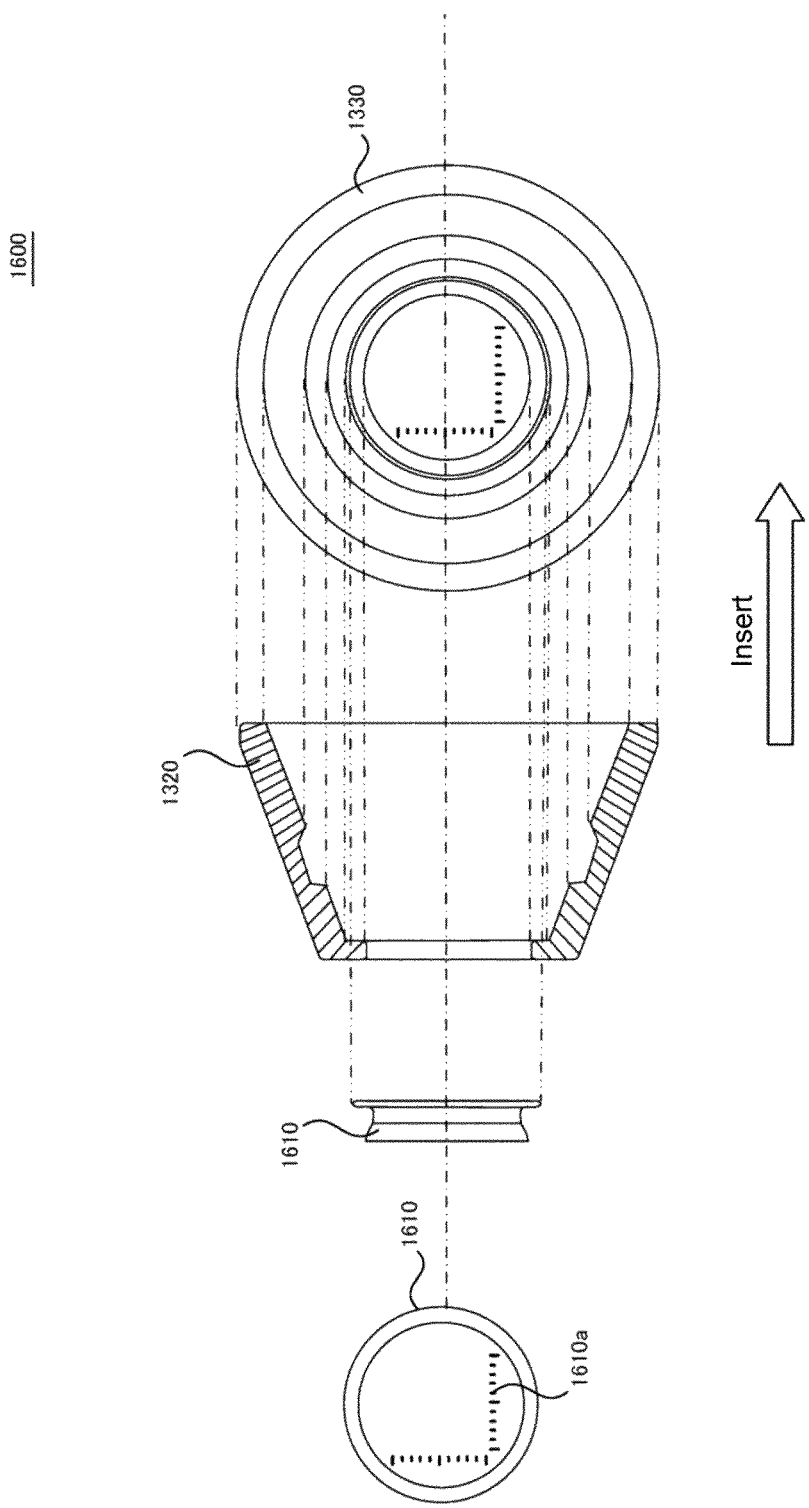
FIG. 16 shows an illustrative diagram of a scale 1600 of the embodiment.

A constitution of the scale 1600 of the embodiment will be further detailed with using FIG. 16. The scale 1600 may be constructed by inserting the scale member 1610 into the opening formed on the upper side of the adapter 1320 and holding the scale member 1610 on the adapter 1620. The diameter of the upper side of the scale member 1610 may be the nearly same diameter as that of the upper side opening of the adapter 1620.

Moreover, the diameter of the bottom side of the scale member 1610 may be formed slightly smaller than the diameter of the inner flat part of the adapter 1620, thereby allowing the scale member 1610 to have a surface contact with the tip surface of the inspection module 115 without fail, and to be securely held accurately parallel to a plane formed by the adapter 1320. The adapter 1320 to be used may be that has the same constitution and dimension as described in FIG. 13.

The adapter 1320 may be formed as a nearly hollow truncated corn, the cross-section of which is shown in FIG. 16. FIG. 16 also shows the inner structure of the adapter 1320 in association with the bottom. The adapter 1320 may be formed with a soft material such as opaque silicone resin, may hold the scale member 1610 at its one end while being mounted on the tip of the truncated corn-shaped inspection module 115 at the other end, thereby allowing to detachably hold the scale member 1610 with frictional resistance of the material constituting the adapter 1320.

The inner surface of the adapter 1320 may have a thinner part circumferentially formed for reducing frictional resistance at insertion/removal. Furthermore, the end of the adapter 1320 may have an opening formed for holding the scale member 1610, thereby detachably holding the scale member 1610 with a concave part formed between the upper surface and bottom surface of the scale member 1610.

On the other hand, the larger diameter end of the holder 1320 may have a tapered shape attachable to the tip of the truncated corn shape on the inspection module 115, thereby holding the scale part 1610 to the imaging device 116 with fastening the scale part 1610 to be attached closely to the tip part of the inspection module 115.

A function of the scale 1600 of the embodiment will now described. The scale 1600 may be constructed by inserting the optically colorless, transparent scale member 1610 into the opaque silicone rubber adapter 1620. Upon imaging a tissue affected part, the imaging device 116 may image the scales 1610a of the scale 1610 with the affected part, thereby allowing a physician to directly obtain the size of the affected part from the image.

Figure 17:
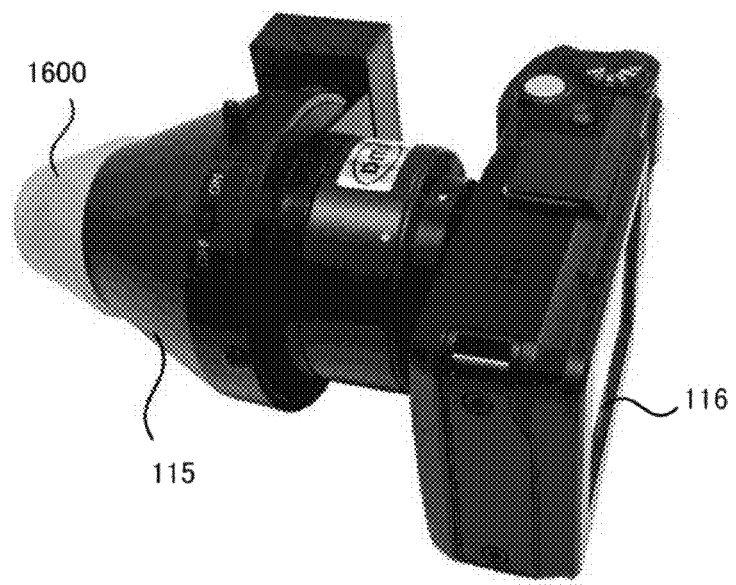
FIG. 17 shows an embodiment of the scale 1600 of the embodiment mounted on the inspection device 100.

FIG. 17 shows an embodiment in the case of the scale 1600 of the embodiment mounted on the inspection device 100. The scale 1600 may be used mounted on the tip part of the inspection module 115 of the imaging device 116. When the scale 1600 is used, the scale 1600 may be disposed closely to an affected part. As the imaging device 116 images an affected part, the scale 1610 may also enter into the image, thereby allowing for obtaining the size of the affected part from the image. In addition, the scale 1600 may be detachable from the inspection module 115 mounted on the imaging device 116, and thus may be able to be divided into the scale 1610 and adapter 1320 after use and to be sterilized with ethanol or the like.

The light guide 1300 and the scale 1600 of the present embodiment may be used with mounted on the inspection module 115 if needed by a physician or the like, thereby improving availability of the inspection device of the embodiment. Furthermore, the adapter 1320 may also be used mounted on the tip of the inspection module 115 without the light-guide member 1310 or the scale 1610 mounted thereon in observation of a tissue. The adapter 1320 mounted on the tip of the inspection module 115 may allow to reduce pressure to capillary vessels or the like adjacent to an affected part, thereby providing an observation with less change of blood flow.

Although the present invention have been described with reference to the embodiments of the present invention, the invention is not limited to the aforementioned embodiment, and provides alteration such as another embodiment, addition, modification, and deletion within the scope which may be contemplated by one skilled in the art. Any aspect may fall within the scope of the present invention as long as it provides an action or effect of the present invention.

INDUSTRIAL APPLICABILITY

According to the present invention, the present invention allows for tissue tissue inspection in the vicinity of the surface which is comparable with use of a conventional echo gel type module and polarization filter module without keeping any inspection module away from the tissue, and also enable to provide an inspection device with improved data accuracy, and a control method and system of the inspection device.

REFERENCE SIGNS LIST

100: inspection device
100*b*: site
101: protection member
102: circular polarization filter
102*a*: polarization state-regulating part
103: LED holder
103 *a*: LED
104: objective lens
105: lens optics system
106: imaging device
107: adapter
110: filter-holding part
110*a*: knob
111: filter-holding member
112: magnet
113: magnet
114: battery package
115: inspection module
115*a*: housing
120: image sensor
201: optical axis
401: light
402: light
500: tissue
601: protection film
602: polarizing plate
603: ¼ wave length plate
604: protection film
610: tissue
710: eyepiece part
711: concave lens
1000: inspection system
1001: patient
1002: affected part
1002*a*: site
1002*b*: site
1010: information-processing device
1020: storage device

The invention claimed is:

1. An inspection device comprising:
an imaging device, and
an inspection module for allowing the imaging device to obtain a tissue image,
wherein the inspection module comprises:
an objective lens for focusing reflected light originated from a tissue to the imaging device,
a plurality of LEDs that surround the optic axis of the objective lens and expose light to the tissue,
a circular polarization filter comprising polarization state-regulating parts disposed in a path of the reflected light for exposing the light from the LEDs to the tissue directly or as a circular polarized light, and
an alignment mechanism for aligning the polarization state-regulating parts with the position of the LEDs,
wherein the circular polarization filter functions as a light isolator for observing reflection light from a skin by actuating the alignment mechanism to align the polarization state-regulating parts at a position making the light from the LEDs as the circular polarized light.

2. The inspection device of claim 1, further comprising a fastening mechanism for relatively fastening the polarization state-regulating parts against the housing of the inspection module during an inspection.

3. The inspection device of claim 1, wherein the inspection device alternates between a direct mode and a polarization mode in a tissue inspection with the alignment mechanism, and takes tissue images in the direct mode and the polarization mode without positional displacement.

4. A tissue inspection system comprising:
the inspection device of claim 1, and
an information-processing device connected to the inspection device so as to allow for intercommunication,
wherein the information-processing device records a first digital image of the tissue generated by exposing directly light of LEDs as is from the LED to the tissue and a second digital image generated at a same position by exposing the light of the LEDs to the tissue after making the LEDs light as circularly polarized light with linking the images to personal identification information.

5. An inspection module for obtaining a tissue image comprising:
an objective lens for focusing a reflected light originated from the tissue to the imaging device,
a plurality of LEDs that surround the optical axis of the objective lens and expose light to the tissue,
a circular polarization filter comprising polarization state-regulating parts disposed in a path of the reflected light for exposing the light from the LEDs to the tissue directly or as a circular polarized light, and
an alignment mechanism for aligning the polarization state-regulating parts with the position of the LEDs, wherein the circular polarization filter functions as a light isolator for observing reflection light from a skin by actuating the alignment mechanism to align the polarization state-regulating parts at a position making the light from the LEDs as the circular polarized light.

6. A light guide for taking an image of a small tissue region, comprising:
a truncated corn-shaped adapter that fits to the shape of the tip of the inspection module of claim 5, and
a light-guide member held in the adapter,
wherein the light-guide member comprises a light guiding part that allows LED light to transmit therethrough and allows reflected light from a tissue to transmit therethrough, and a base part that is continuous to the light guiding part and contacts with the inspection module and
wherein an outer surface from the light guide part to the base part is processed as frosted glass.

7. A scale for measuring the size of an affected part comprising:
a truncated corn-shaped adapter that fits to the shape of the tip of the inspection module of claim 5, and
a scale member that is held in the adapter and contacts with the inspection module,
wherein the scale member allows LED light to transmit therethrough and allows reflected light from a tissue to transmit therethrough and comprises optically detectable scales for measuring the size of the affected part.

8. A method of controlling an inspection device comprising:
an imaging device, and
an inspection module for allowing the imaging device to take tissue images in a direct mode and a polarization mode at a same tissue position,
the method comprising: adjusting the position of polarization state-regulating parts formed in a circular polarization filter through the inspection module positioned on a tissue, exposing light of LEDs directly from the LEDs to the tissue, and recording a first digital image; and
readjusting the position of the polarization state-regulating parts formed in the circular polarization filter, exposing the light of the LEDs to the tissue after making the LEDs light as circularly polarized light, and recording a second digital image.

9. The control method of claim 8, comprising altering the amount of light of the LED for recording the first digital image and the digital image.

* * * * *